United States Patent [19]

Stewart et al.

[11] Patent Number: 5,084,160

[45] Date of Patent: Jan. 28, 1992

[54] METHOD FOR SOLUBILIZATION OF LOW-RANK COAL USING LOW MOLECULAR WEIGHT CELL-FREE FILTRATES DERIVED FROM CULTURES OF CORIOLUS VERSICOLOR

[76] Inventors: Dorothy L. Stewart, 2304 Muriel Ct., Richland, Wash. 99352; James K. Fredrickson, 32007 Alhambra Rd., Kennewick, Wash. 99336; James A. Campbell, 5504 W. Melville, Pasco, Wash. 99301; John W. Pyne, Jr., 1788 Jackson Rd., Carmel, Ind. 46032; Roger M. Bean, 2212 Benton, Richland, Wash. 99352; Bary W. Wilson, 34011 Caballo Rd., Kennewick, Wash. 99337

[21] Appl. No.: 317,263

[22] Filed: Feb. 28, 1989

[51] Int. Cl.$^5$ ............................................. C10G 1/04
[52] U.S. Cl. .................................. 208/428; 44/620; 44/628; 44/608; 208/400; 252/1; 435/68.1; 435/822; 530/500; 530/300; 530/344
[58] Field of Search .............. 435/68.1; 208/428, 400; 44/50, 620, 628

[56] References Cited

U.S. PATENT DOCUMENTS

| | | |
|---|---|---|
| 2,907,389 | 10/1959 | Hitzman . |
| 3,826,308 | 7/1974 | Compere-Whitney . |
| 3,844,348 | 10/1974 | Stratton . |
| 3,937,520 | 2/1976 | Sievert . |
| 3,982,995 | 9/1976 | Yen et al. . |
| 4,085,972 | 4/1978 | Ghosh et al. . |
| 4,640,767 | 2/1987 | Zajic et al. . |
| 4,659,670 | 4/1987 | Stevens, Jr. et al. . |
| 4,846,964 | 7/1989 | Scott et al. ........................ 208/428 |

OTHER PUBLICATIONS

Koide et al.–Chem. Abst. vol. 108 (1988), p. 73820a.

Primary Examiner—Sam Rosen

[57] ABSTRACT

A method is provided for isolating a less than 5,000 dalton molecular weight extracellular product from *Coriolus versicolor*. The extracellular product is useful for biosolubilizing low-rank coals to form water-soluble products.

15 Claims, 1 Drawing Sheet

METHOD FOR SOLUBILIZATION OF LOW-RANK COAL USING LOW MOLECULAR WEIGHT CELL-FREE FILTRATES DERIVED FROM CULTURES OF CORIOLUS VERSICOLOR

The present invention is directed to a method for solubilizing low-rank coals with low molecular weight cell-free filtrates derived from *Coriolus versicolor*, which results in a water-soluble product useful as a fuel or fuel additive. The present invention also provides a method for producing the cell-free filtrates for this purpose.

BACKGROUND OF THE INVENTION

In nature, white-rot fungi, known lignin degraders, use plant matter as a source of nutrients, whereas the majority of microorganisms that live on plant matter do not degrade lignin. It is believed that lignin is a precursor of low-rank coals. A number of white-rot fungi are able to degrade low-rank coals as reported in the literature. See Cohen, *et al.*, *Applied Environmental Microbiology*, 44: 23-27 (1982); Wilson, *et al.*, *Proceedings of the Tenth Annual EPRI Contractors Conference on Coal Liquefaction*, May 6, 1986, Palo Alto, CA. Scott, *et al.*, *Biotechnology Progress*, 2, 131-139 (1986); and Cohen, *et al.*, *Proceedings of the Direct Liquefaction Contractors Meeting*, U.S. Department of Energy: Washington, D.C.; pages IV-48 to IV-64 (1986). The process of solubilizing low-rank coal with white-rot fungi has been termed "biosolubilization", indicating the metabolic origin of the soluble product. Work on biomineralization using German hard coals has been reported by Fakausa, Ph.D. thesis, Fredrich-Wilhelms University, Bonn, Federal Republic of Germany (1981); and the literature of bioconversion of coals, its relation to lignin degradation and work of lignin has been reviewed by Pyne and Wilson; *Biological Coal Beneficiation Literature Review*, Battelle Pacific Northwest Laboratory Report to the Electric Power Research Institute, May 1986.

Pyne et al., *Appl. Environ. Microbiol.* 53: 2844-48 (1987), have shown that an extracellular product from *C. versicolor* can biosolubilize leonardite and that this product was produced in conjunction with an oxidative enzyme, laccase (syringaldezine oxidase), which is also produced by the fungus. Initial purification of the extracellular product by ultrafiltration procedures indicated the product molecular weight is between 10,000 and 100,000, as disclosed in commonly assigned copending Ser. No. 69,709, filed July 6, 1987.

We have now found that the major portion of the coal solubilizing activity in the cell-free filtrates of *C. versicolor* is contained in the low molecular weight fractions of less than 5000 daltons, and particularly in the range of 500-1000 daltons. We have also found that the active coal solubilizing materials are likely to be siderophore-like which solubilize coal by a chelation mechanism.

It is therefore an object of the present invention to provide a method for producing low molecular weight cell-free filtrates of *C. versicolor* which are capable of biosolubilizing low-rank coals.

It is a further object of the present invention to provide a method for biosolubilizing low-rank coals to a soluble product using low molecular weight cell-free filtrates of *C. versicolor*.

These and other objects of the present invention will be readily apparent from the following description, appended claims and by practice of the invention described herein.

SUMMARY OF THE INVENTION

The present invention provides a method for isolating molecular weight extracellular products derived from a culture of *Coriolus versicolor* comprising the steps of separating the cells from a broth of *C. versicolor* to obtain a cell-free filtrate, separating from the cell-free filtrate a fraction containing molecules of molecular weight less than 5000 daltons, preferably in the range of 1000 to 500 daltons. These active fractions may be utilized to degrade low-rank coal into a water soluble material.

DESCRIPTION OF THE PREFERRED EMBODIMENTS

Figure 1:
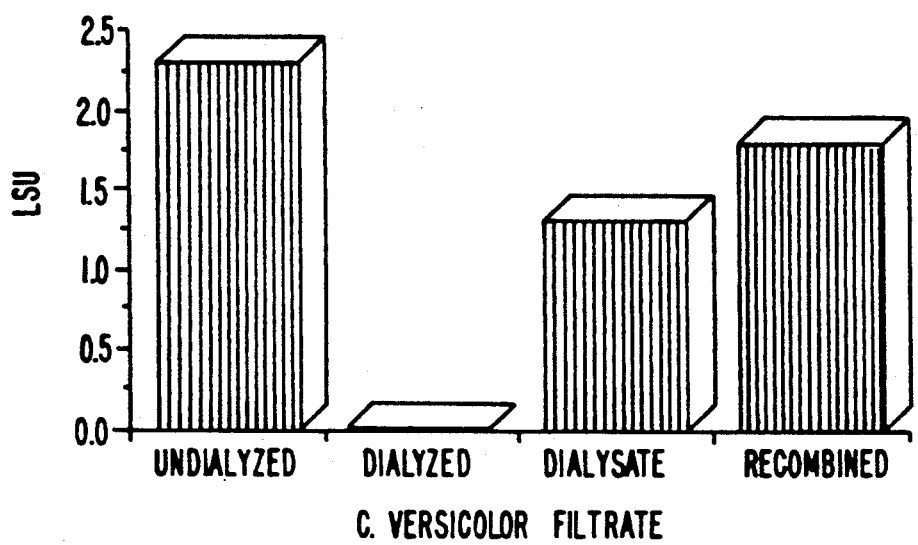
FIG. 1 is a graph of coal biosolubilization activity of cell-free filtrates from *C. versicolor* with leonardite.

The present invention is applicable to a process for treatment of low-rank coals and coal processing by-products, meaning those types of soft coals having high lignite content. Examples of such coals include leonardite and those coals generally characterized as lignites. The microorganism cultures from which the extracellular product with which the present invention is practiced derived from common white-rot fungi *Coriolus versicolor* (ATCC Deposit No. 12679), also known as *Trametes versicolor* and *Polyporus versicolor*.

The coals utilized in accordance with the present invention may be untreated, but are preferably pretreated by any one of the following methods in order to improve the microbial degradation. The low-rank coals may be pretreated with nitric acid and hydrogen peroxide in accordance with procedures disclosed by Scott, *et al.*, *Biotechnology Progress* 2: 131-139 (1986). A particularly preferred pretreatment process is to expose the coal at temperatures above about 100° C. (most preferably at about 150° C.) for approximately seven days.

Prior to treatment with the extracellular liquid having biosolubilization activity, the coal may be washed and sized, if desired, to improve its adaptability to the particular bioreactor apparatus utilized. This sizing procedure will be readily determinable by those of ordinary skill in the art. A stock culture of *C. versicolor* may be routinely maintained, for example, in 5% Sabouraud maltose broth (30° C., 84-98% RH, pH 5.6). When needed, the culture may be grown to increase levels of the extracellular enzymes which have biosolubilization activity. Conditions for growing *C. versicolor* are known in the art, for example, a growth medium may be used such as that described by Fahraeus, *et al. Acta Chemica Scandinavica* 2367-2378 (1967). The fermentation may be initiated with an inoculum of *C. versicolor* grown on Sabouraud maltose broth for seven to ten days at 25. with no agitation. The lignite coal may also be sterilized prior to fermentation by using irradiation and/or autoclaving to decrease the risk of contamination of the cell culture. The fungi grown under these conditions form a mycelial mat. The mats may be transferred to a vessel containing distilled water and a stirring apparatus (such as glass beads) and shaken vigorously, then the mycelial fragments may be transferred to the fermentor. To enhance the levels of the requisite extracellular enzymes (believed to have laccase-like activity), 2,5-xylidine may be added to the fermentor after about three days growth to increase extracellular enzyme production according to the procedure set forth by Fahraeus, et al., supra.

Typically the extracellular fluid formed during growth may be separated from the cell mass by filtration (sometimes referred to as the cell-free filtrate), such as by filtering through several layers of a sieve-like material, such as cheesecloth, or other common filtration devices. The coal solubilizing activity is primarily in the compounds contained within this cell-free broth having molecular weight less than 5000 daltons and particularly within the range of 1000 to 500 daltons. As an initial screen, it will be convenient to dialyze the cell-free broth with a dialysis material having a molecular weight cut-off of 10,000 daltons. Typically, this dialysis may be conducted in a buffer, such as phosphate buffer, particularly 0.5 M phosphate buffer. The cell-free filtrate will typically have coal solubilizing activity as determined, for example, by the leonardite solubilizing assay described below. After dialysis with a 10,000 dalton cut-off, the filtrate may then be successively filtered through appropriate ultrafiltration filters having cut-offs of 5000, 1000 and 500 daltons.

The most active fraction, and the preferred fraction for use in the present invention, is that fraction containing materials having a molecular weight from 1000 to 500 daltons. Typically this fraction will be characterized by leonardite coal biosolubilizing activity (in leonardite solubilizing units, LSU, defined as mg. coal solubilized per ml. of filtrate per 24 hrs. at room temperature) of at least about 40% of the leonardite coal biosolubilizing activity of the cell-free filtrate. A second fraction having molecular weight materials in the range of 5000 to 1000 daltons will typically have a leonardite coal biosolubilizing activity of about 20% of the leonardite coal biosolubilizing activity of the cell-free filtrate. Finally, the fraction containing molecules having molecular weights of 500 or less will typically have a leonardite coal biosolubilizing activity of at least 10% of the leonardite coal biosolubilizing activity of the cell-free filtrate.

The active fractions containing the coal solubilizing activity coelute with laccase activity, which may be measured using syringaldazine as a substrate (Bolag, et al., Applied and Environmental Microbiology 48: 849–854 (1984)). However, laccase activity is not the only indicator of coal-solubilizing activity, since commercially prepared laccase from Asoeroillus oryzae (Sigma Chemical Co.) does not solubilize coal in vitro.

The cell-free solubilizing-active preparation may be mixed with untreated low-rank coal (or with low rank coal prepared in any one of the methods described above, such as treatment for sterilization, granulation, oxidation, autoclaving, etc.) The cell-free preparation and the low-rank coal will be incubated together until the coal is solubilized. The respective amounts of cell-free preparation and coal will be readily determinable by those of ordinary skill in the art an will include consideration of such factors as the solubilizing activity of the particular preparation utilized, the type and method of preparation of the coal, the size of the run, configuration of apparatus utilized to contact the coal with the cell-free preparation, and the like.

The duration of incubation of the cell-free preparation with the coal will vary. Usually solubilization will be evident after about 24 hours of contact and, depending on the size and particular conditions of the incubation, complete solubilization may be obtained by incubation up to approximately 2 weeks.

Although not necessary, for convenience, the resulting biodegraded product may be precipitated with acid (usually by bringing the biodegraded mixture to about pH 2 with a mineral acid such as hydrochloric acid). A typical acid-precipitated, digested-coal product (from a cell-free extract of C. versicolor) has somewhat controllable solubility characteristics due to the exchange of counterions by the acid precipitation. A soap-like product may be obtained by increasing, for example, the sodium counterion concentration, thereby rendering the product useful as an energy-rich surfactant to enhance the quality of coal/water slurries. Also, ion exchange may remove unwanted trace metals and provide more desirable counterions.

Uses of the biosolubilized coal product include its use as a polar liquid-soluble additive for blending with fuels as an extender. For example, the biosolubilized product may be blended with short chain alcohols to make a diesel fuel substitute. The process of solubilizing coals may be utilized for mining of thin-seam or marginal coal reserves which are presently uneconomical to mine and transport. These marginal coal reserves may be biosolubilized *in situ* (in the ground or in shallow pits) and then recovered by pumping the liquified material to the surface.

The biosolubilized material may also be utilized as a feedstock for acid-catalyzed methylation to produce high-quality fuels.

The biosolubilized product may also be used as a source for value-added chemicals, such as surfactants or bioactive compounds, whereby these chemicals would be separated from the raw biosolubilized product and the residue used as a fuel.

Having described the invention and the preferred embodiments thereof, the following examples are provided by way of illustration. However, the following examples are not intended to nor should they be construed as imposing a limitation on the invention.

EXAMPLE 1

An extracellular product is obtained from *C. versicolor* as follows. The inoculum comprises three 50 ml culture of *C. versicolor* grown on Sabouraud-maltose broth (Cohen, et al., Appl. Environ. Microbiol., 44, 23–27 (1982)) for 7 to 10 days at 25° C. with no agitation. The fungi grown under these conditions forms a mycelial mat. The mats are transferred to a stopped vessel containing 250 mls distilled water and 50 mls of 3 mm glass beads. This vessel is shaken vigorously and the mycelial fragments are transferred to the fermentor. The fungus is grown in a Chemap CF-20 fermentor at 25° C., and was supplied with 4 L. of filtered air per minute at atmospheric pressure to 15 L. of the growth medium published by Fahraeus, et al. (Acta Chem. Scan. 21, 2367–78(1967)). A two-stage Rushton turbine (6-blade) agitator system is used at a speed of 400 R.P.M. After three days growth in the fermentor, 0.3 ml of 2,5-xylidine (Aldrich Chemical, Milwaukee, WI) is added to increase levels of extracellular polyphenol oxidase. The extracellular fluid formed during the growth is separated from cell mass by filtration through several layers of cheesecloth.

The in vitro assay for biological conversion of coal 30 consisted of incubating ground coal (150–200 micrometers) with extracellular material as obtained above. Although several coals could be solubilized *in vitro*, the coal used in routine assays was leonardite obtained from American Colloid Co. (Skokie, IL.) The total volume of the assay mixture was 1 ml and contained 100 micromoles sodium phosphate at pH 5.2 and 10 mg of leonardite. The assay mixture was typically incubated for 20 minutes at 23° C. (room temperature) with occasional manual agitation. After incubation the mixture was briefly centrifuged in a desktop clinical centrifuge for 30 seconds to separate the coal from the liquid. An aliquot of the supernatant was removed, diluted in water and its absorbance at 290 nm measured with a spectrophotometer. This assay was modified for the unfractionated filtrate by reading the absorbance at 450 nm and incubating for 24 hours at room temperature. This assay method became the standard assay method for the experiments.

EXAMPLE 2

A cell-free filtrate from *C. versicolor* was dialyzed with tubing having a 10000 dalton cut-off. Twenty-three ml of concentration (4×) filtrate was dialyzed for 48 hours against 0.5 M phosphate buffer with three changes of buffer, 200 ml each. After dialysis was complete, the dialyzed filtrate (>10,000 M.W.) was collected and stored at −20° C. All dialysates were pooled, lypholized, and adjusted to original starting volume. Leonardite conversion assays were used to measure activity of the undialyzed filtrate, the dialyzed filtrate, dialysate, and the combination of the dialyzed filtrate and the dialysate. Results of these assays are presented in FIG. 1 as leonardite solubilizing units (LSU). These results indicate that most of the coal biosolubilizing activity is associated with the dialysate (<10,000 M.W.) than in the dialyzed filtrate (>10,000 M.W.). The leonardite conversion assay is described in Example 1.

EXAMPLE 3

To further define the molecular weight range of the leonardite-biosolubilizing *C. versicolor* component, approximately 100 ml of active filtrate was filtered sequentially through membranes with the molecular weight cutoffs of 10,000, 5000, 1000, and 500 using an Amicon ultrafiltration apparatus. Both the retentate and the filtrate from each filtration were adjusted to the original starting volumes. Approximately 10% of the starting volume remained after each filtration step. All retentates and filtrates were assayed for coal biosolubilization. These results are presented in FIG. 2 and are expressed as percent coal conversion and indicate that most of the biosolubilizing activity is present in the 500–1000 M.W. range.

Figure 2:
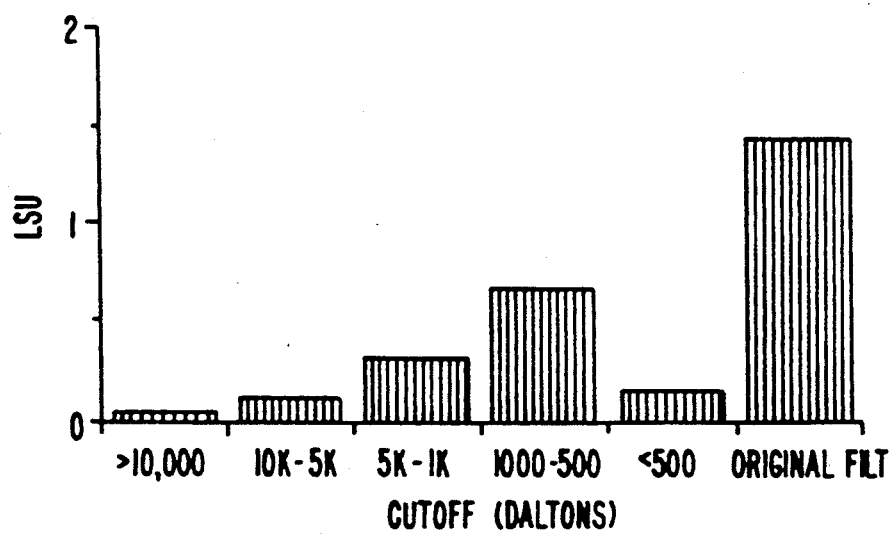
FIG. 2 is a graph of coal biosolubilization activity of various cell-free fractions of *C. versicolor* filtrates of molecular weights less than 10,000 daltons.

As shown in FIG. 2, the original filtrate has a leonardite solubilizing activity of about 1.4 LSU. The 1000 to 500 dalton fraction has an activity of about 45% of that value, the 5000 to 1000 dalton fraction has an activity of about 22% of that value, and the >500 dalton fraction has an activity of about 12% of that value.

Gel permeation chromatography

A sample of 20× *C. versicolor* culture filtrate was applied to a Sephadex G-50 (fine) column, 2.6×26 cm. The column was eluted with 0.05 M 2,2 dimethylsuccinic acid (pH 5.5) and 2 ml fractions collected. Absorbance of each fraction was read at 280 nm to identify protein and/or amino acid-containing fractions. Fractions with syringealdezine oxidase activity were also identified. Coal biosolubilizing activity was measured using the standard leonardite solubilization assay. Both the peak absorbance and the peak leonardite solubilizing activity have similar patterns of elution. The syringealdezine oxidase appears at the beginning of the 280 nm absorption peak and is limited to less than five fractions. However, these syringealdezine oxidase fractions had little coal solubilizing activity.

To more closely approximate the molecular weight of the *C. versicolor* active fraction, molecular weight standards were eluted on the Sephadex G-50 column. A calibration curve, defined as the relationship between the elution volumes of a set of molecular weight standard proteins and the logarithm of their respective molecular weights, was determined. The elution parameter used for the calibration was $K_{av}$. This parameter is calculated as follows:

$$K_{av} = \frac{Ve - Vo}{Vt - Vo}$$

where
Ve = elution volume for the protein or unknown sample
Vo = column void volume = elution volume for Blue Dextran 2000
Vt = total bed volume The standards, Ovalbumin (43,000 daltons), Chymotrypsinogen (25,000 daltons) and ribonuclease A (13,700 daltons) were used to determine the calibration curve. The $K_{av}$ for the active fraction is larger than the standard proteins, indicating that the molecular weight is less than 1000. Although this value is extrapolated outside the range of the standards, the value obtained is in agreement with and confirms the ultrafiltration and dialysis molecular weight determinations for the active fraction.

EXAMPLE 4

To further characterize the active fraction we conducted experiments to denature the most active (1000–500 daltons) fraction by heating at 100° C. for 40 minutes. Both heated and unheated fractions were assayed for coal activity. Biosolubilizing activity of the heated fraction was not reduced by this treatment. Thus, this active component is probably not an enzyme since most enzymes are irreversibly denatured by this treatment.

EXAMPLE 5

A procedure for the isolation of the components responsible for the biosolubilization activity similar to that previously published by Teintze et al. (*Biochemistry*, 20: 6446–56 (1981)) was used for purification of a known siderophore, pseudobactin. Approximately 1 g of ferric nitrate was added to a liter of filtrate and the suspension was saturated with ammonium sulfate. The resulting slurry was extracted with benzyl alcohol and further treated by using a previously described procedure by Neilands (J.A.C.S., 74: 4846–47 (1952)). The red-brown aqueous extracts were concentrated to dryness in vacuo below room temperature. The residue was dissolved in a mixture of pyridine and acetic acid, and the resulting solution was adjusted to pH 5.5. Two bands were separated and the predominant red-brown band was concentrated to dryness. The residue was dissolved in 10 ml of pyridine and 30 ml of water. The resulting solution was then chromatographed at 4° C.

on a column (5×100 cm) containing Bio-Gel P-2 (200–400 mesh, Bio-Rad Laboratories), equilibrated in 0.2 M pyridine-acetic acid, pH 7.4. The red-brown band was concentrated to dryness, and the residue was stored at 4° C. away from light. Approximately 0.1 g of the residue was dissolved in 3 ml of water, and the UV spectrum of this solution was obtained with a Varian DMS 200 UV visible spectrophotometer.

Approximately 0.5 g of the red-brown residue was deferrated with 8-hydroxyquinoline as described previously by Meyer and Abdallah (J. of Genet. Microbiol. 107, 319–328 (1978)). After the yellow-green aqueous extract was concentrated to dryness, the residue was dissolved in 5 ml of 0.2 M pyridine-acetic acid buffer, pH=5.5, and the resulting solution was chromatographed on a column containing bio-Gel P-2 equilibrated in the same buffer. A yellow-green band was collected and concentrated to dryness. Approximately 0.1 g of the residue was dissolved in 3 ml of water and analyzed with a Varian DMS 200 UV spectrophotometer.

Desferal mesylate (Ciba-Geigy Corporation, Pharmaceuticals Division, Summit, N.J.), a natural product that complexes iron was used to compare its properties with the above separated material. Approximately 0.2 g of the desferal mesylate was dissolved in water and ferrated in the same manner as discussed above. A UV spectrum of the ferrated material was obtained. The ferrated component was then deferrated with 8-hydroxyquinoline and a UV spectrum obtained. Both the iron complex and deferrated complex of desferal mesylate and the ferrated and deferrated complex from C. versicolor were also tested for coal biosolubilization activity.

The ferrated and deferrated complexes from C. versicolor gave absorption maxima at 430 and 360 nm, respectively. These absorption maximum compare favorably with other Fe siderophores. As an example, the Fe complex of pyoverdine showed a maximum absorbance at approximately 420 nm and the pyoverdine had a maximum at about 380 nm. Pseudobactin was very soluble in water; an aqueous solution of the chloride salt at pH 7.2 had an absorption maximum at 400 nm with a shoulder at 385 nm. The ferrated and deferrated desferal mesylate complexes show absorption maxima at 424 and 370 nm, respectively. It appears from the preliminary results that the complexing chemical produced by C. versicolor may be similar to that of desferal mesylate.

Fractions collected from the Bio-Gel P-2 column described above were assayed for coal biosolubilization before deferration. Approximately 380 mg of dried fraction #2 was dissolved in 2 ml of distilled water and assayed using the standard leonardite coal assay. A sample of fraction #1, less than 10 mg dry weight, was also assayed. All fractions were adjusted to pH 5.5. Fraction #2 showed the most leonardite solubilizing activity with an LSU value of 1.74, while fraction #1 had an LSU value of 0.2. According to the siderophore purification procedure, fraction #2 is the one that should contain the siderophore-like component. Ferric sulfate (10 mM) added to the coal assay reaction mixture significantly reduced the coal solubilizing activity of this fraction, suggesting that not all of the C. versicolor siderophore was complexed with $Fe^{+3}$. Thin layer chromatographs of fraction #2 indicate that a number of ninhydrin-positive components are still present in this fraction, these are likely amino acids or short peptides. Peptides and amino acids are known to be able to complex metals and may be competing with the siderophore for $Fe^{+3}$. Leonardite biosolubilizing assays were also conducted on deferrated fractions collected from the Sephadex G-25 column used in the siderophore purification procedure. No measurable coal activity was observed. Also, coal assays conducted on desferal mesylate which had been ferrated and deferrated showed no biosolubilizing activity. Apparently the deferration procedure destroyed the coal solubilizing activity.

It is claimed that:

1. A method for isolating a extracellular product derived from a broth of Coriolus versicolor comprising the steps of: separating the cells from a broth of C. versicolor to obtain a cell-free filtrate; separating from said cell-free filtrate a fraction containing molecules of molecular weight in the range of about 500 to 1000 daltons.

2. A method according to claim 1 wherein said fraction is characterized by leonardite coal biosolubilizing activity in LSU of at least about 40% of the leonardite coal biosolubilizing activity of said cell-free filtrate.

3. A method for isolating an extracellular product derived from a broth of Coriolus versicolor comprising the steps of: separating the cells from a broth of C. versicolor to obtain a cell-free filtrate; separating from said cell-free filtrate a fraction containing molecules of molecular weight in the range of about 5000 to 1000 daltons.

4. A method according to claim 3 wherein said fraction is characterized by a leonardite coal biosolubilizing activity in LSU of at least about 20% of the leonardite coal biosolubilizing activity of said cell-free filtrate.

5. A method for isolating in an extracellular product derived from a broth of Coriolus versicolor comprising the steps of: separating the cells from a broth of C. versicolor to obtain a cell-free filtrate; separating from said cell-free filtrate a fraction containing molecules of molecular weight in the range of less than about 500 daltons.

6. A method according to claim 5 wherein said fraction is characterized by a leonardite coal biosolubilizing activity in LSU of at least about 10% of the leonardite coal biosolubilizing activity of said cell-free filtrate.

7. A method for degrading low-rank coal to a water-soluble material comprising the step of contacting said low-rank coal with a cell-free fraction from the broth of Coriolus versicolor containing molecules in the molecular weight range of about 500 to 1000 daltons.

8. A method for degrading low-rank coal to a water-soluble material comprising the step of contacting said low-rank coal with a cell-free fraction from the broth of Coriolus versicolor containing molecules in the molecular weight range of 5000 to 1000 daltons.

9. A method for degrading low-rank coal to a water-soluble material comprising the step of contacting said low-rank coal with a cell-free fraction derived from the broth of Coriolus versicolor containing molecules in the molecular weight range of less than about 500 daltons.

10. A solubilized coal product produced according to the process of claim 7.

11. A solubilized coal product produced according to the process of claim 8.

12. A solubilized coal product produced according to the process of claim 9.

13. A cell-free extract of C. versicolor produced according to the process of claim 1.

14. A cell-free extract of Coriolus versicolor produced according to the process of claim 3.

15. A cell-free extract of Coriolus versicolor produced according to the process of claim 5.

* * * * *

UNITED STATES PATENT AND TRADEMARK OFFICE
CERTIFICATE OF CORRECTION

PATENT NO. : 5,084,160
DATED : January 28, 1992
INVENTOR(S) : Dorothy L. Stewart, et al It is certified that error appears in the above-identified patent and that said Letters Patent is hereby corrected as shown below:

Column 2, line 6: "molecular weight" should read
--low molecular weight--

Column 2, line 36: "and Polvporus versicolor" should
read --and Polyporus versicolor--

Column 2, line 60: "*Scandinavica* 2367-2378" should read
--*Scandinavica 21:* 2367-2378--

Column 2. line 62: "ten days at 25." should read
--ten days at 25°-

Column 3, line 51: "from *Asoeroillus oryzae*" should
read --from *Aspergillus oryzae*--

Column 3, line 61: "in the art an will" should read
--in the art and will--

Signed and Sealed this

First Day of June, 1993

Attest:

MICHAEL K. KIRK

*Attesting Officer*   Acting Commissioner of Patents and Trademarks

UNITED STATES PATENT AND TRADEMARK OFFICE
CERTIFICATE OF CORRECTION

PATENT NO. : 5,084,160

DATED : January 28, 1992

INVENTOR(S) : Stewart, et. al.

It is certified that error appears in the above-indentified patent and that said Letters Patent is hereby corrected as shown below:

On the cover page add:

[73] Assignee: Electric Power Research Institute, Inc.
     Palo Alto, California Attorney, Agent, or Firm should read —Flehr, Hohbach, Test, Albritton & Herbert—.

Signed and Sealed this

Fourteenth Day of December, 1993

Attest:

BRUCE LEHMAN

Attesting Officer

Commissioner of Patents and Trademarks